US011534284B2

(12) United States Patent
Schumacher et al.

(10) Patent No.: US 11,534,284 B2
(45) Date of Patent: Dec. 27, 2022

(54) EMBOLIC PROTECTION DEVICE, FOLDING METHOD AND FORMING DEVICE

(71) Applicant: Protembis GmbH, Aachen (DE)

(72) Inventors: Oliver Schumacher, Aachen (DE); Michael Pfennig, Aachen (DE); Victor Alfonso Jimenez Diaz, Vigo Pontevedra (ES); Conrad Rasmus, Berlin (DE); Karl Von Mangoldt, Cologne (DE)

(73) Assignee: Protembis GmbH, Aachen (DE)

( * ) Notice: Subject to any disclaimer, the term of this patent is extended or adjusted under 35 U.S.C. 154(b) by 124 days.

(21) Appl. No.: 16/345,369

(22) PCT Filed: Sep. 18, 2017

(86) PCT No.: PCT/EP2017/001097
§ 371 (c)(1),
(2) Date: Apr. 26, 2019

(87) PCT Pub. No.: WO2018/077458
PCT Pub. Date: May 3, 2018

(65) Prior Publication Data
US 2019/0307545 A1   Oct. 10, 2019

(30) Foreign Application Priority Data

Oct. 28, 2016   (DE) .......................... 102016012869.0

(51) Int. Cl.
*A61F 2/01*   (2006.01)

(52) U.S. Cl.
CPC ................ *A61F 2/01* (2013.01); *A61F 2/011* (2020.05); *A61F 2002/016* (2013.01)

(58) Field of Classification Search
CPC ...... A61F 2/01; A61F 2/013; A61F 2002/011; A61F 2002/016; A61F 2230/0008; A61F 2230/0076; A61F 2/011
See application file for complete search history.

(56) References Cited

U.S. PATENT DOCUMENTS

| | | |
|---|---|---|
| 8,460,335 B2 | 6/2013 | Carpenter |
| 2010/0179583 A1* | 7/2010 | Carpenter ............... A61F 2/013 606/200 |
| 2010/0324589 A1 | 12/2010 | Carpenter et al. |
| 2013/0103075 A1 | 4/2013 | Wang et al. |
| 2014/0074148 A1 | 3/2014 | Glenn et al. |
| 2014/0163603 A1 | 6/2014 | Zajarias |

(Continued)

FOREIGN PATENT DOCUMENTS

| | | |
|---|---|---|
| EP | 2859864 A1 | 4/2015 |
| JP | 2010-526583 A | 8/2010 |

(Continued)

*Primary Examiner* — Melanie R Tyson
(74) *Attorney, Agent, or Firm* — Michael J. Brown

(57) ABSTRACT

Embolic protection device for insertion into an aortic arch, with a filter unit, a frame and a feed unit, wherein the filter unit is arranged at the frame and the frame provides a proximal area having a proximal shape, which is arranged in an inner area of the frame and is connected to the feed unit, wherein the proximal shape has a first part and a second part, wherein the second part is formed at one end of the first part.

15 Claims, 14 Drawing Sheets

(56) References Cited

U.S. PATENT DOCUMENTS

Figure 1:
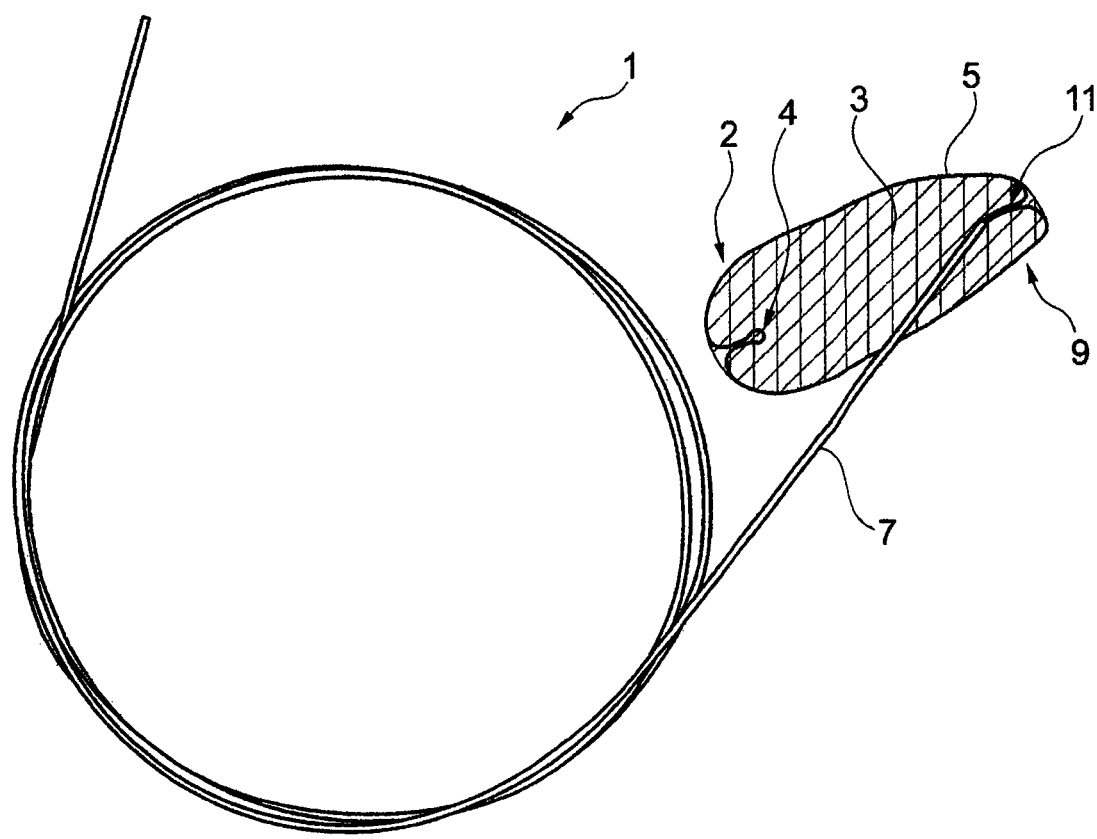

| | | | | |
|---|---|---|---|---|
| 2015/0313701 | A1* | 11/2015 | Krahbichler | ............... A61F 2/01 |
| | | | | 606/300 |
| 2016/0175084 | A1 | 6/2016 | Johnson et al. | |
| 2016/0302909 | A1* | 10/2016 | Kelly | ...................... A61F 2/013 |
| 2016/0324621 | A1* | 11/2016 | Shezifi | ...................... A61F 2/01 |

FOREIGN PATENT DOCUMENTS

| | | | |
|---|---|---|---|
| JP | 2012-501704 | A | 1/2012 |
| JP | 2016-533228 | A | 10/2016 |
| RU | 2518457 | C2 | 6/2014 |
| RU | 2599592 | C2 | 10/2016 |
| WO | 2008-137177 | A2 | 11/2008 |
| WO | 2010-026240 | A1 | 3/2010 |
| WO | 2015-055605 | A1 | 4/2015 |
| WO | 2015/177322 | A1 | 11/2015 |

* cited by examiner

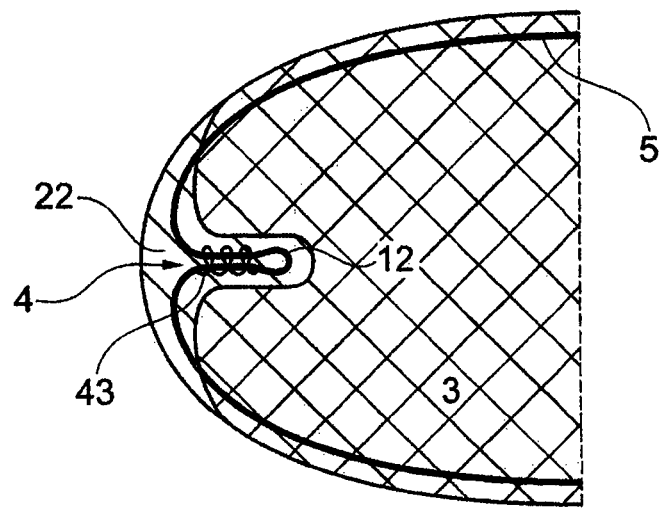
Fig. 12
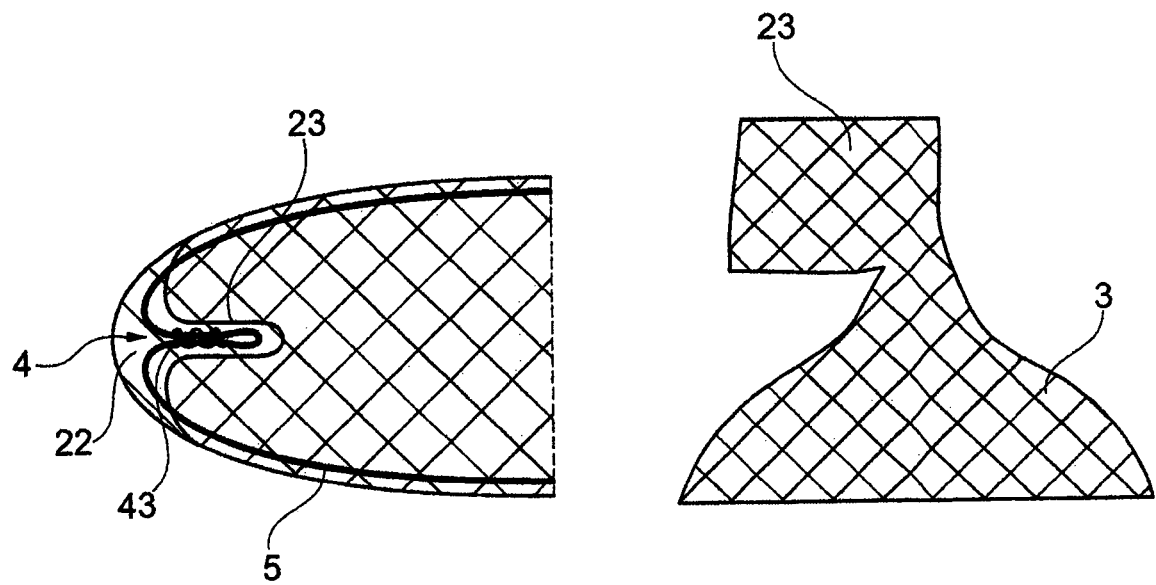
Fig. 13
Fig. 9

EMBOLIC PROTECTION DEVICE, FOLDING METHOD AND FORMING DEVICE

The invention relates to an embolic protection device according to the preamble of claim 1 which prevents undesirable macroscopic particles out of a blood stream from entering one or more branch vessels of a main blood vessel, such as the aortic arch. The invention also relates to a forming device for shaping the inventive embolic protection device, as well as a method for folding and unfolding the inventive embolic protection device by means of the forming device.

Cerebral embolism is a known complication in heart surgery and in interventional cardiology. Particles can be loosened by surgical or interventional operations. They can enter the blood stream and, in particular, trigger an embolism in the brain. If a cerebral embolism happens, it can cause a stroke or even death.

Embolic protection devices are known, for example, from the applicant's EP2859864.

It is an object of the present invention to provide an improved embolic protection device so that in a simple manner undesirable macroscopic particles from a blood stream are prevented from entering one or more branch vessels of a main blood vessel.

The inventive solution is achieved by the features the independent claims. Further advantageous developments of the invention are provided by the dependent claims.

According to a first aspect of the invention an embolic protection device for insertion into an aortic arch is provided, comprising a filter unit, a frame and a feed unit, wherein the filter unit is arranged at the frame. The frame provides a proximal area comprising a proximal shape, which is arranged in an inner area of the frame and is connected to the feed unit, wherein the proximal shape comprises a first part and a second part, wherein the second part is formed at one end of the first part.

The inner area of the frame comprises both the plane spanned by the frame as well as the area below or above this plane.

The inventive embolic protection device provides in an advantageous manner a device which is characterised by a spring mechanism created by the connection of the proximal shape and the feed unit, which provides that the embolic protection device is pressed on to the wall of the blood vessel in the aorta in the direction of the head vessels substantially in the distal area. Undesirable macroscopic particles are substantially deflected using the embolic protection device.

The proximal area is positioned in front of the ostium of the left subclavian artery by retracting the feed unit. Thus a stable position is achieved in the aortic arch. In an alternative positioning scenario, the embolic protection device can also be inserted via the right subclavian artery. In this case, the proximal area is positioned in front of the ostium of the brachiocephalic artery by retracting the feed unit.

The spring mechanism is formed in particular by the geometry of the proximal shape. Preferably, the first part of the proximal shape is arranged below the plane of the frame, in particular in the inner area of the frame. The first part is advantageously formed in the shape of an arch. The second part of the proximal shape is arranged preferably above the frame, in particular in the inner area of the frame. The second part is advantageously formed straight. Preferably, the first and the second part are at an angle to one another and/or to the plane of the frame. In other words, at least the first and/or the second part(s) may be arranged above or below the plane of the frame, wherein the angle between the first part and the plane of the frame differs from the angle between the second part and the plane of the frame, so that the first and the second part enclose an angle.

Using the feed unit, the proximal shape can be brought under tension, so that the spring effect is transmitted via the proximal shape to the entire frame of the embolic protection device. Due to this tension transmission, the distal area of the frame in particular folds up.

The frame of the embolic protection device extends over a two dimensional plane and changes in the proximal area into a proximal shape, which advantageously can protrude from this plane downwards or upwards. The proximal shape arranged inside the frame and connected with the feed unit creates the spring mechanism, which ensures that the frame with the filter unit can be secured over one or more blood vessels, so that they are protected or covered. When the filter unit is spread, radial forces take effect. The positioning of the embolic protection device is performed by the spring mechanism and by the feed unit. Furthermore, a haptic feedback is achieved when positioning the embolic protection device or a resistance is felt when retracting of the feed device so that, accordingly, the correct position of the embolic protection device can be checked. In particular, the head blood vessel by which the embolic protection device is introduced is also covered and protected.

Because of the geometry of the frame, in particular the proximal shape and/or the distal shape, the embolic protection device adapts itself flexibly to the anatomical conditions in the aortic arch regardless of the entry path and offers a complete coverage of all head blood vessels.

Advantageously, the first part and the second part of the proximal shape are arranged in the inner area of the frame. In particular, the connection point between proximal shape and feed unit is arranged in the inner area of the frame so that the coverage of the entry blood vessel is ensured. In other words, the proximal area of the frame or, respectively, of the filter unit covers the ostium of the entry blood vessel and extends far beyond it. At the same time, the proximal area of the frame or, respectively, of the filter unit is in contact with the aorta wall. In particular, therefore, this ensures coverage of the entry blood vessel when the embolic protection device is placed in the aortic arch.

The inventive embolic protection device, in particular the frame and the filter unit arranged on it, can be completely folded and unfolded. In the folded state, the embolic protection device is preferably dimensioned such that its diameter is substantially 1.4-2.2 mm, in particular 1.7-1.8 mm. The embolic protection device has three states: an unfolded state, in which the embolic protection device is in its basic form (basic state), a folded state, for example, in a catheter (folded state), and an unfolded state (placement state), when the embolic protection device is used as intended, such as in the aortic arch in the final position. The final position in the aortic arch is also called the placement position in the following.

The geometric form of the three states is different. During transportation and preparation for implantation, the embolic protection device is in its basic state, as shown, for example, in the figures. Due to mechanical reshaping, the basic state is converted into the folded state. The reversibly deformable material of the frame, for example, a superelastic nitinol wire, can be reshaped so that the embolic protection device can be pushed into a catheter. In doing so, the embolic protection device is extended along its direction, wherein, by folding up the distal shape and the proximal shape into an outer area of the frame, it changes into a straight or extended shape. The consequent change in length depends on the reduction in the width. In this case, the folded frame, i.e. the two sides of the frame outside the distal shape and/or proximal shape, are located from the tip to the end of the frame, that is, from the distal shape to the proximal shape, parallel to each other in the catheter. The specially attached filter unit is able to follow this mechanical deformation and is located in the intermediate space between catheter and wire. The frame made of nitinol provides a so-called shape memory effect.

In the placement position in the aortic arch, the geometry of the frame of the embolic protection device flexibly adapts to the aorta wall and lies in a slight arc, following the curvature of the aorta, in front of the head blood vessel outflows. When leaving the catheter, both the distal shape as well as the proximal shape folds back into their original shape, thus enabling an atraumatic positioning of the frame at the aorta wall. Due to the specific shape of the folded distal shape and proximal shape, transitions or corners with sharp edges are avoided. Radial forces generated by the shape memory effect of the frame, span the filter surface. Extra frame stability is achieved by the physiological conditions in the aorta since, due to the surface resistance of the filter, the blood flow additionally presses the frame of the embolic protection device into its placement position.

The material of the frame is preferably nitinol. The frame can be a wire, or a hollow wire in whose hollow space a platinum-/platinum-iridium-/tantalum wire is placed, wherein the hollow space is almost completely filled. Alternatively, the frame can be made from DFT wire, for example, from Fort Wayne Metals, or can be a wire with a firmly attached platinum/tantalum core. These examples for the material of the frame have the advantage that the frame is radiopaque.

The filter unit comprises a filter material which is selectively permeable so that, for example, undesirable macroscopic particles from the blood stream cannot enter into one or more branch vessels of a main blood vessel, such as the aortic arch. For example, the filter material comprises different materials, such as plastics or metallic materials such as nitinol. It is possible, depending on the material used, to weave, cast, laser-cut or to stamp the filter material. Preferably the filter material is a woven membrane made of polyamide. The filter material preferably has a pore size of 40-150 μm and an open porosity of 35-60%, by means of which it ensures, on the one hand, good protection from undesirable particles and, on the other hand, good porosity for blood. The filter material can have square or rectangular open surfaces. The thickness of the filter material is preferably 20-120 μm.

The feed unit is a tube made of wound stainless steel wire, but other materials can be chosen also. The feed unit is resistant to kinking and serves, when positioning the embolic protection device, to transmit torque and force. Advantageously, the length of the feed unit is 120-250 cm with a diameter of 1.5 mm and has a plastic coating externally (pebax coating, polyethylene (PE), polytetrafluorethylene (PTFE), polyamide (PA)).

The length of the embolic protection device is advantageously 50 to 100 mm. The width of the embolic protection device is advantageously 15 to 45 mm.

In a further development, the embolic protection device provides that the first part of the proximal shape is at a first angle to the plane of the frame and the second part is at a second angle to the first part of the proximal shape. Advantageously, the first and second parts of the proximal shape are aligned coaxially at the connecting point between first and second parts and form the spring mechanism by varying the sizes of the angles via the feed unit, so that the embolic protection device can be secured in the placement position in the aortic arch. The first part of the proximal shape is at an angle of about 25 to 50 degrees, preferably 30 degrees, downwards to the two-dimensional plane of the frame, measured from the first part to the plane. The first part is straight or arc-shaped and preferably has a length of 0.5 to 2.5 cm cm. The second part, preferably straight in shape, is formed at the end of the first part. The second part encloses a second angle of preferably 80 to 115 degrees with the first part, measured from the second part to the first part. If the second angle is measured to the two-dimensional plane of the frame, it is substantially 110 to 145 degrees, measured from the second part to the plane. Preferably, the second part is substantially 1-5 cm long. This geometric shape of the proximal shape ensures that the geometry of the proximal shape in the positioned state is such that it adapts to the anatomy.

Another advantageous further development provides that the proximal shape comprises two ends of the frame which extend parallel to each other in the inner area of the frame. This makes the frame more stable longitudinally as well as laterally. In further developments of the embolic protection device, the two ends are attached to the feed unit by means of an adhesive bond. The ends of the wire are not freely accessible therefore. Further developments are also possible in which the proximal shape comprises only one end of the frame wherein the second end of the frame is attached, for example, to the feed device.

In advantageous further developments, provision is made that the frame has a distal area which comprises a distal shape, which is arranged in an inner area of the frame. Advantageously, the tip of the distal shape is coated with atraumatic material (such as membrane material, polymer, rubber or resin adhesive) so that atraumatic protection is provided. Advantageously, this material can be formed as a nose in the shape of a droplet.

In another advantageous further development, the distal shape is characterised such that it provides a constriction towards the inside of the frame. The constriction serves as a connection place for the filter unit. It also serves as an aid to positioning in the aorta since it is provided with radiopaque markers and can be used advantageously as a means for displaying the alignment of the frame in the catheter. The distal shape arranged in the inner area of the frame serves, furthermore, in an advantageous manner as an aid to positioning when pushing the embolic protection device through a forming device into a catheter. In this process, the distal shape can be hooked on to or into the forming device and be folded in the direction opposite that of the original direction. In other words, the distal shape can be folded outwards, that is, into an area outside the inner area of the frame. The advantage of this is that, when pushing through a catheter, for example, the frame can be arranged space saving in the catheter. By folding the distal shape, torsional forces are transferred to the frame, which result in the folding back of the distal shape in the inner area of the frame when unfolding the embolic protection device in the aortic arch.

Advantageously the joint between frame and filter unit is an adhesive tunnel connection. The adhesive tunnel connection is made as an enveloping polymer shape around the frame. In other words, the adhesive envelopes the frame in the shape of a tube or cylinder. The polymer shape forms a so-called adhesive tunnel, in which the frame is arranged and can move relative to the latter. Advantageously, the joint between the adhesive tunnel and the filter unit can also be mechanically stable. By separating the filter unit from the frame, flexibility is created in the distal and proximal areas, which enables, or at least facilitates the folding of these areas when folding or unfolding the embolic protection device.

In another advantageous further development, provision is made that the filter unit is connected to the frame outside the proximal and/or distal area(s). This connection is mechanically stable, that is, with no relative movement between adhesive and frame. Advantageously the connection is formed as a flexible joint. For example, the joint can be a glue joint, a form fit, a weld or a sewn joint. The adhesive tunnel enables a stable and flexible connection to be made also or in particular during the folding or unfolding of the embolic protection device.

In a further advantageous further development, the filter unit in the distal area is connected with the frame substantially as far as the constriction. This prevents the filter unit from unintentionally folding down underneath the frame. The connection can be formed up to the start of the constriction.

In another advantageous further development, the filter unit in the proximal area is connected to the frame substantially up to the first part of the proximal shape. The connection can be made up to the start of the first part.

In another advantageous further development, the filter unit in the distal and proximal areas is connected flexibly to the frame. Therefore, this enables a relative movement to be made between frame and filter unit. This ensures that the frame in the proximal and distal areas is connected movably with the filter unit. In contrast, the frame in the remaining area is connected immovably to the filter unit.

Advantageously, this connection is an adhesive tunnel connection which is made as an enveloping polymer shape around the frame. For an adhesive tunnel connection, the frame is immersed in an adhesive. During drying of the adhesive, the adhesive is moved and forms a polymer shape on the filter unit (like a tube). Geometric changes of the embolic protection device, in particular of the frame, for example, when folding or unfolding the frame or, respectively, the filter unit, can be carried out easily, thus avoiding a delay or, in the most extreme case, damage to the embolic protection device.

Preferably the frame is connected to the filter unit with prestressing. For example, the slightly pressed frame can be connected to the filter unit in order to maintain a prestressing. The connecting of the filter material to the frame is preferably arranged such that the frame, both in the basic state as well as in the positioned state, applies a prestress to the filter unit.

Advantageously, the filter unit is glued to the frame from below. The result is that a smooth surface is created for the flow of blood.

In an advantageous further development, the edge of the filter unit is sealed before attachment to the frame to prevent changes in shape as it is being used, as well as effecting as atraumatic an interaction with the aorta wall as possible.

In another advantageous further development, provision is made that the filter unit protrudes over the frame. Preferably, the filter unit protrudes outside the proximal and/or distal area(s). The protrusion of the filter unit over the frame outside the distal or proximal areas is advantageously between 0.5 and 2.0 mm wide, so that a sealing lip is formed to the vessel wall when the frame is positioned in the placement state in the aortic arch. The sealing lip supports an atraumatic placement of the frame as well as the stability of its shape. Additionally, this sealing lip in the placement state closes against the aorta wall, thus preventing leakage, such as through a valve, around the sides of the embolic protection device.

Advantageously the protrusion is sealed, providing a smooth closure of the filter material. This also supports the atraumatic placement of the frame.

In another advantageous further development, provision is made that the filter unit in the proximal and/or distal area(s) of the frame is flipped over the frame from the lower side to the upper side. Thus the filter unit protrudes into the outer area of the frame. Due to the flipping or turning over/folding over of the filter unit over the proximal and/or distal area(s) of the frame, the attachment of the filter unit on the frame is improved, wherein the complete covering of all head blood vessels is ensured when the embolic protection device is positioned in the aortic arch. The filter unit is located in the proximal and/or distal area(s) as a double layer, thereby increasing the effectiveness of the filter.

In another advantageous further development, the filter unit in the distal and/or proximal area(s) is secured by means of a thread, yarn or wire to the distal shape or proximal shape. Additionally, this connection can be sealed to achieve a stable shape. Furthermore, due to the sealing, the connection in this area is atraumatic.

In an advantageous further development, the filter unit is secured to the distal shape by gluing. The gluing can be achieved by means of a resin adhesive. Due to the gluing, the frame has an atraumatic tip in the distal area, so if contact is made with the distal area with, for example, the aorta wall, it is protected from injuries.

Advantageously the filter unit is attached in the proximal area by means of a coil. The coil is made of stainless steel wire which wraps the ends of the frame preferably in the shape of a spiral. The coil serves to stabilise the connection between filter unit and feed unit. In addition, the coil shape supports the change in shape during of the folding and unfolding of the embolic protection device.

In order to improve the embolic protection device even further, it is provided in an advantageous further development that the filter unit is made of a fibre material wherein the fibres are aligned in such a way that they are at an angle of substantially 45 degrees with a longitudinal axis of the frame. The fibre material consists of a woven membrane which ensures that it has increased flexibility in the longitudinal and lateral directions of the frame. The longitudinal direction of the frame extends from the proximal to the distal area and is preferably the centre line of the frame. Preferably, the oblique orientation of the fibres forms an angle of 45±10 degrees to the longitudinal axis of the frame.

In another advantageous further development, provision is made that the proximal shape is connected to the feed unit, wherein the two ends of the frame are wrapped by a wire, whose ends are arranged parallel to the ends of the frame. The joining of the proximal shape of the frame to the feed unit is done preferably by means of an adhesive joint. The ends of the frame are inserted into an open lumen of the feed unit where they are glued. The wire which wraps the ends of the frame and consequently secures it, is preferably a stainless steel wire and serves to make the ends of the frame additionally stable. The ends of the wrapped stainless steel wire lie parallel to the ends of the frame wire and are preferably glued together in the feed unit. The transition from the frame wire to the feed unit as well as the wrapped stainless steel wire are preferably sealed flexibly, such as with a polymer mixture, to provide a smooth surface as well as an even transition.

Preferably the frame of the embolic protection device has a basic state in the form of an oval shape. The oval shape matches the native shape of the aortic arch roof and thus enables all three head blood vessels to be covered reliably. The upper area of the aortic arch at this point is shaped like, for example, the inside of an oval, inverted bowl. Thus, by inserting an oval shape, a positive fit is achieved. Preferably, the oval shape is tapered towards the proximal shape. In other words, the cross section through the aorta at the point at which the embolic protection device is placed, is oval so that the oval shape of the frame advantageously adapts to the physiological shape at this point.

According to a second aspect of the invention a forming device for shaping the inventive embolic protection device is provided. The embolic protection device has all or at least some of the mentioned features—they will not be repeated again at this point. The shaping is carried out to feed the embolic protection device into a catheter, wherein the frame of the embolic protection device having the filter unit arranged at it, is transformed from an expanded state to an extended state. The forming device has two subsections which meet at the narrowest cross section. The subsections are each preferably funnel-shaped. The distal subsection is preferably formed as a flat or round funnel and serves as the entrance for the inventive embolic protection device. The proximal subsection is preferably formed as a circular funnel and serves to receive an substantially circular tube, such as a commercially obtainable introducer sheath or a commercially obtainable catheter. The forming device is a tool with a geometry which allows the embolic protection device, in particular its frame, to change its shape in such a way that it has a diameter in the folded state of preferably substantially 1.4-2.0 mm, in particular 1.7-1.8 mm. It is ensured with the forming device that the embolic protection device can be easily put into an substantially circular tube, such as a commercially obtainable introducer sheath or a commercially obtainable catheter.

In a further development, the preferably flat or round opening of the forming device is shaped such that the proximal shape and/or a distal shape of the frame of the embolic protection device can be folded outwards. Amongst other things, this ensures the correct and damage-free introduction of the embolic protection device, for example, into a catheter. In other words, the proximal and/or distal shape (s) which extend(s) in the basic state of the embolic protection device towards the inside of the frame is/are folded in the opposite direction, i.e. outwards, by the flat or round opening.

According to a third aspect of the invention a method for folding the inventive embolic protection device by means of the forming device is provided. The embolic protection device has all or at least some of the mentioned features— they will not be repeated again at this point. The method comprises the steps:
Moving of the frame of the embolic protection device in front of the flat or round opening of the forming device, wherein the feed unit is guided through the forming device;
introducing or retracting the proximal shape into the forming device, wherein the proximal shape is folded outwards;
hooking the distal shape over the outer edge of the distal subsection of the forming device, wherein, by inserting further, the distal shape folds outwards and is inserted into the forming device.

In a further development of the method, it is advantageously provided that, by inserting the frame in the forming device, the frame is pushed together and is extended longitudinally. Due to the tapering shape of the distal subsection of the forming device, the frame is pushed together from both sides so that, when it leaves to enter the narrowest cross section of the forming device, it has a longitudinally extended shape.

In a further development of the method, it is advantageously provided that the embolic protection device is pushed out of the aforementioned tube, containing the folded embolic protection device and which can be, for example, a commercially obtainable introducer sheath, into a catheter placed beforehand in the aortic arch. A hemostasis valve on the proximal end of the catheter serves here to receive and secure the tube and simultaneously to minimise the loss of blood as the placing is taking place. With a forward push on the feed unit, the embolic protection device is now pushed out of the tube into the catheter. As soon as the frame is located completely in the catheter, the tube can be removed and retracted through the feed unit. The embolic protection device can then be pushed by pushing the feed unit forward and out through the distal end of the catheter into the aorta arch.

In another further development of the method, it is advantageously provided that the embolic protection device is pushed out of the aforementioned tube, which can be, for example, a commercially obtainable catheter, into a sheath placed beforehand in the aortic arch. With a push on the tube through the sheath, the embolic protection device in the tube can be pushed to the distal end of the sheath in the aortic arch.

In all further developments of the inventive embolic protection device, provision is made that the folded up proximal shape transfers a prestress to the frame, which is substantially equal to the tension causing the bent proximal shape to be straightened.

Furthermore, a method for unfolding the embolic protection device from a catheter containing it is also provided. The invention also comprises the provision that the embolic protection device can be received in a longitudinal or cylinder-shaped or catheter-like device due, for example, to the method for folding the embolic protection device. When unfolding the embolic protection device out of the catheter, it is first pushed out until the distal area of the frame has left the catheter. With a further push feeding the embolic protection device out of the catheter, the distal shape is pushed out, which folds back into the inner area of the frame. Due to the folding of the distal shape, the frame in the distal area is restored to the prestressed state before the folding of the embolic protection device. The folding of the distal shape serves as an aid to orientation and makes it possible for the frame of the embolic protection device to change shape so that it can be inserted into practically any catheter. Furthermore, the folding of the distal shape is atraumatic.

At its proximal area, the feed unit can have two markings, wherein the first, with later placement of the embolic protection device through the guide catheter, indicates that the distal shape is located directly in front of the exit opening of the catheter and the second marking indicates that the frame has already left the catheter completely.

In a further advantageous further development, the direction of the frame is displayed by one or more markers. The markers can be radiopaque. The markers can be arranged in particular in the distal area of the frame. The distal area indicates the direction of the frame as it is pushed out of the catheter. The advantage of this is that primarily the position of the frame, the direction in which it is being fed and the placement position can be established precisely.

Further details of the invention can be derived from the embodiment examples which are described below with the aid of the figures. Furthermore none of the stated details of the invention are limited to the embodiment examples provided, but, instead, may be represented individually, selectively together or in their entirety in other embodiment examples.

Figure 2:
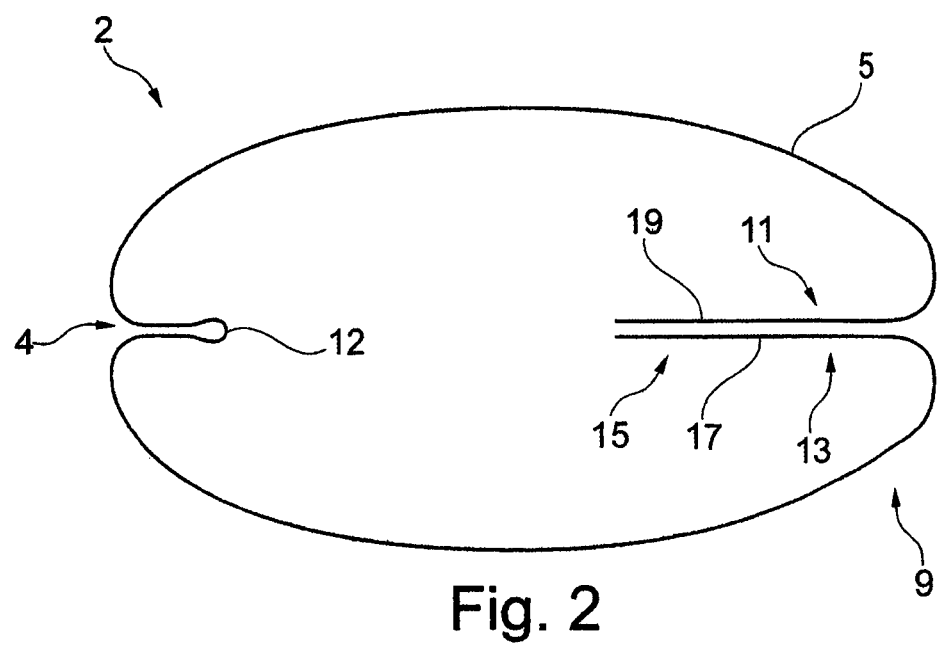
Figure 3:
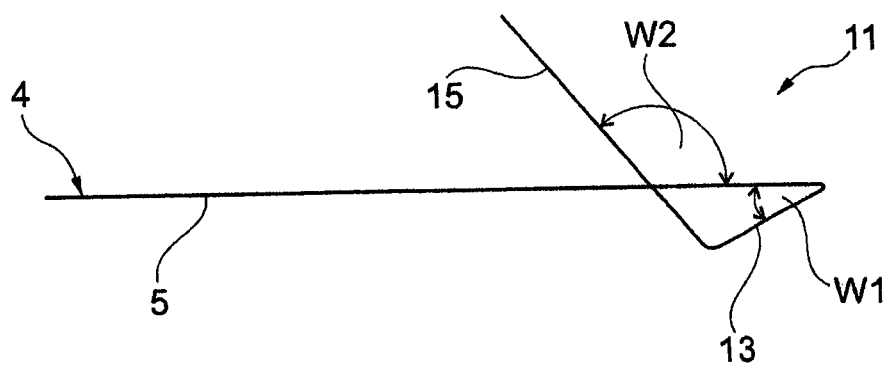
Figure 4:
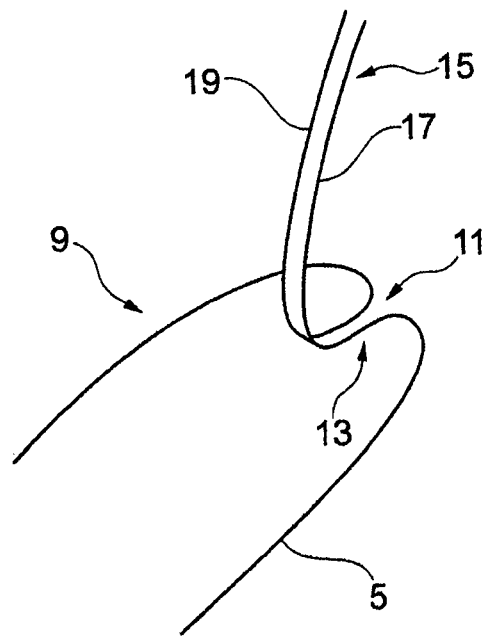
Figure 5A:
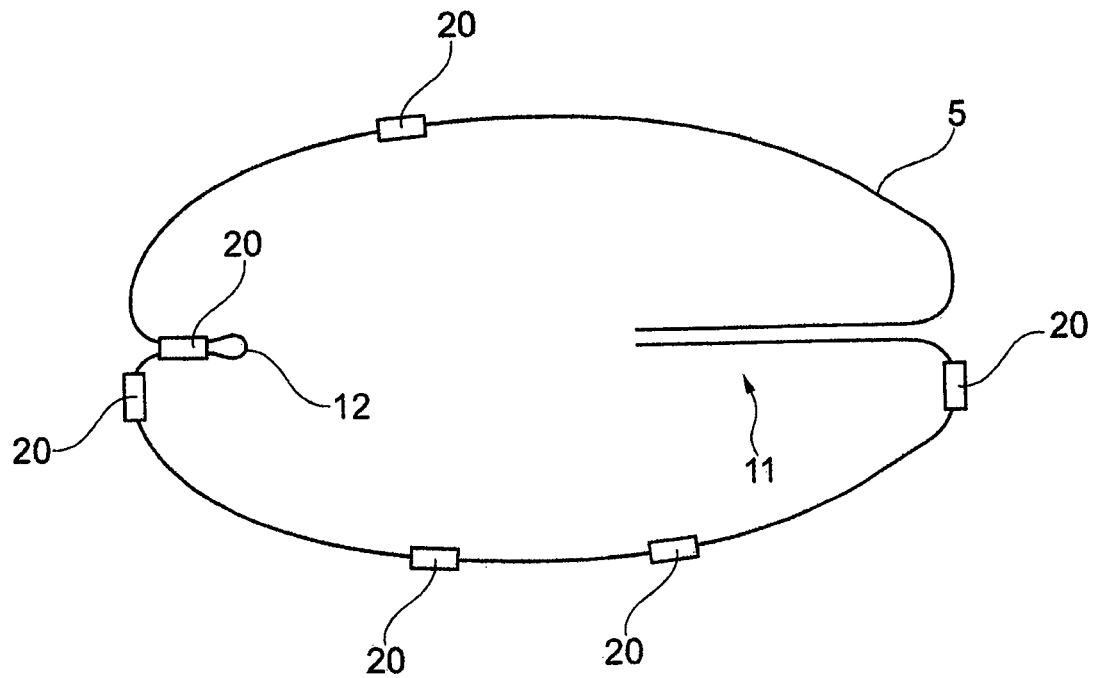
Figure 5B:
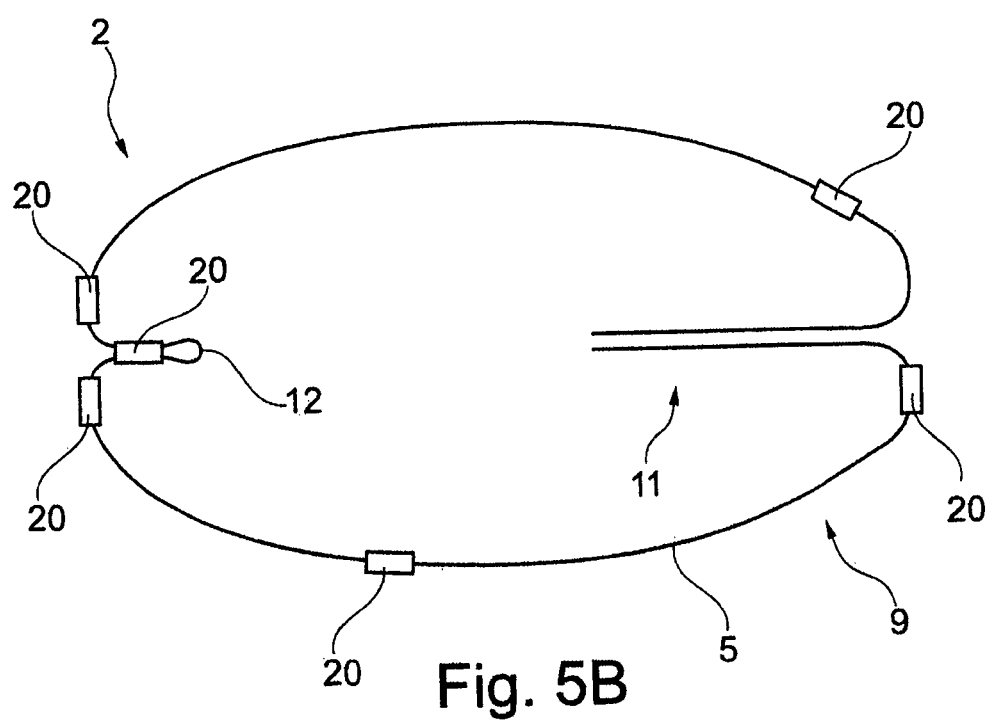
Figure 6:
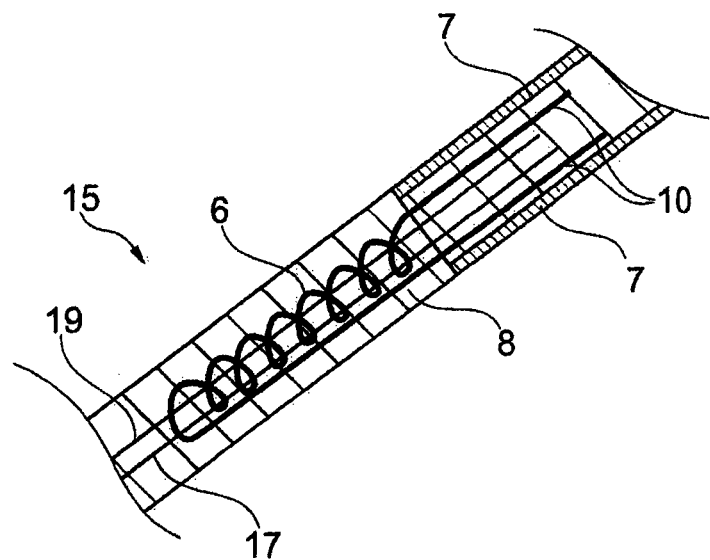
Figure 7:
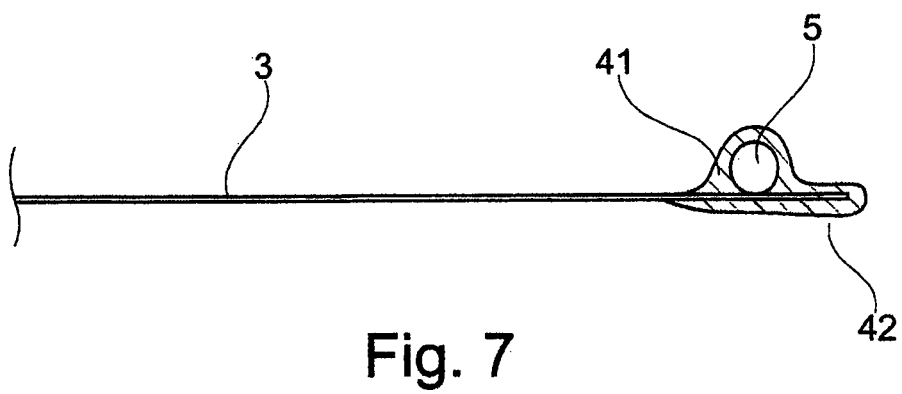
Figure 8:
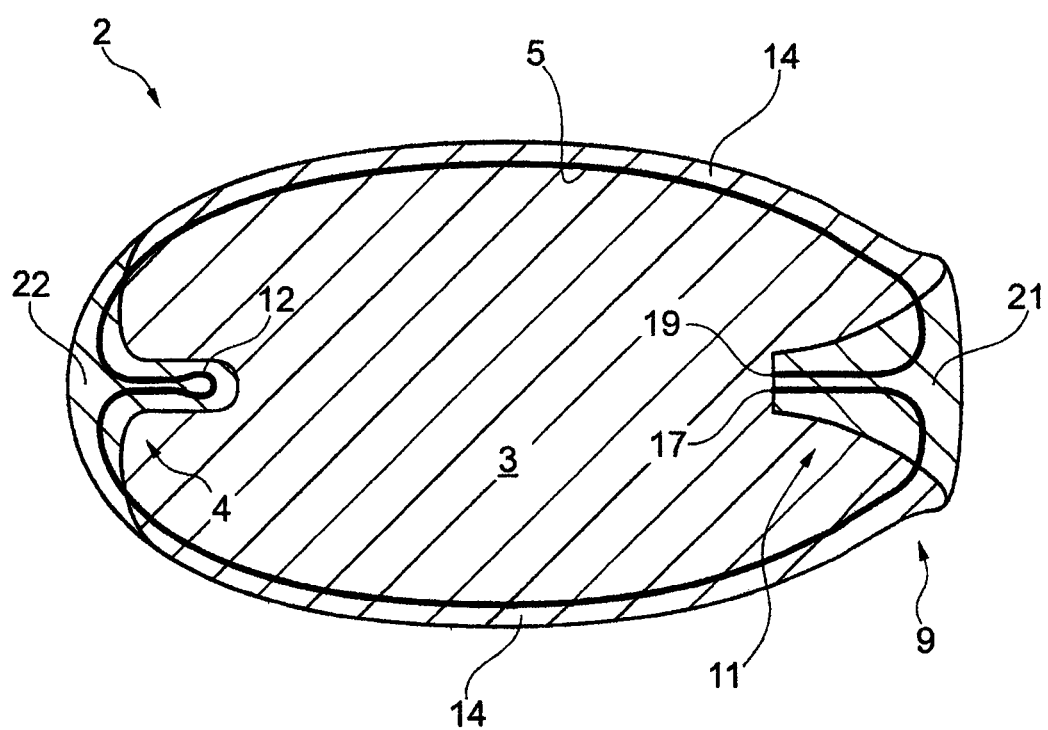
Figure 10:
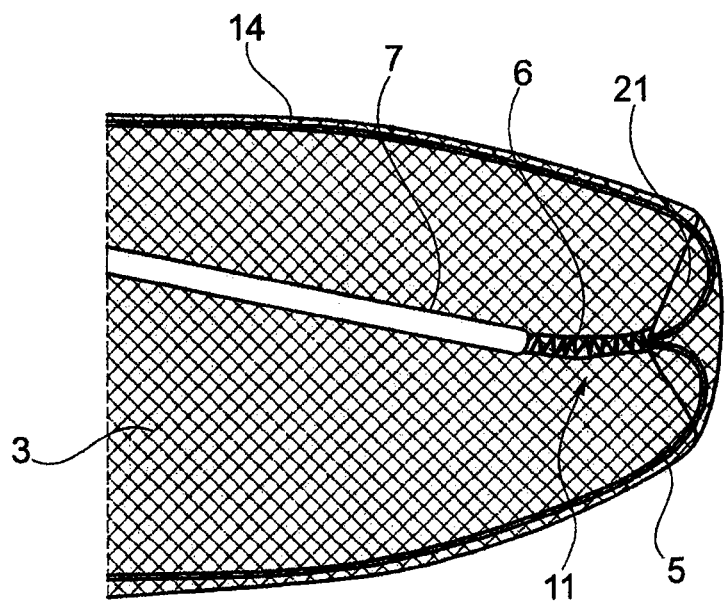
Figure 11:
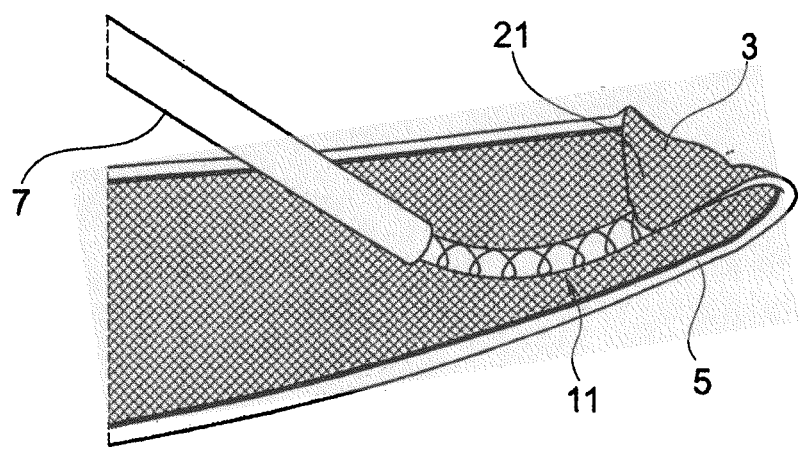
Figure 14:
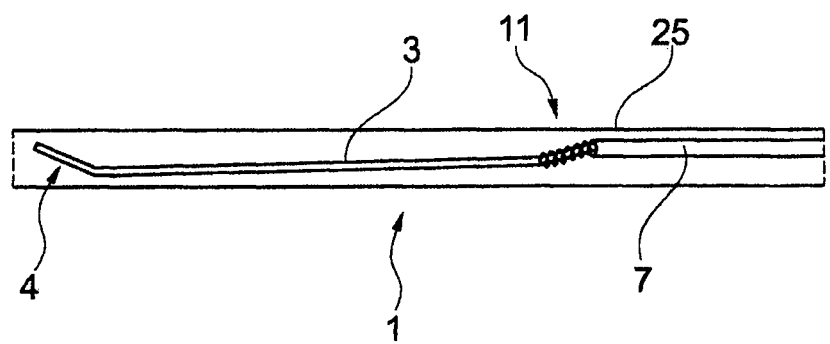
Figure 16:
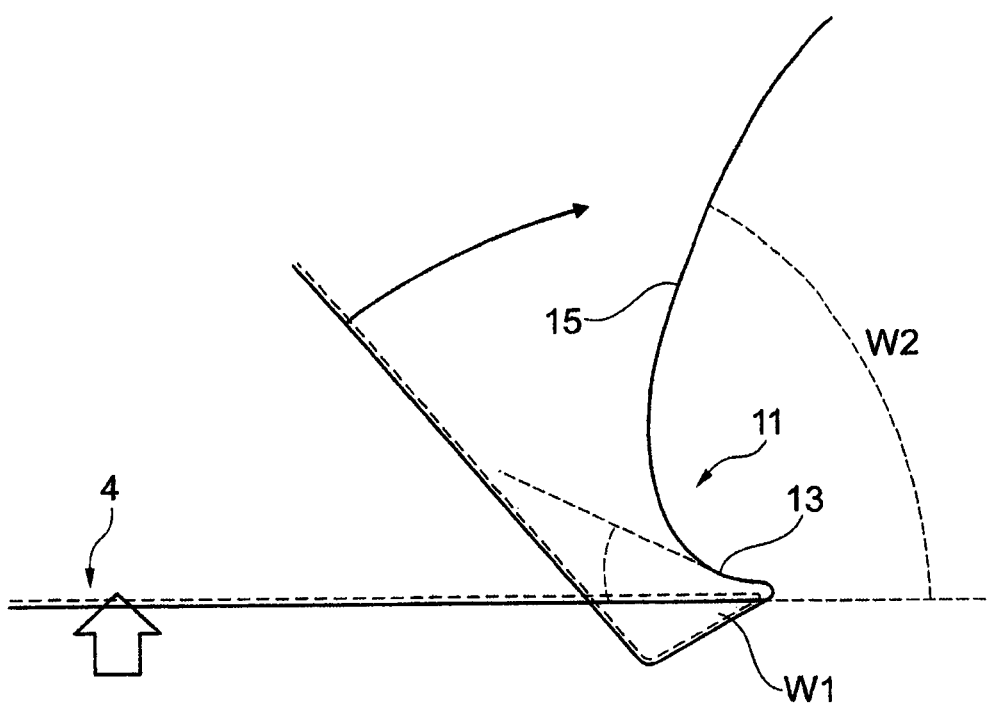
Figure 17:
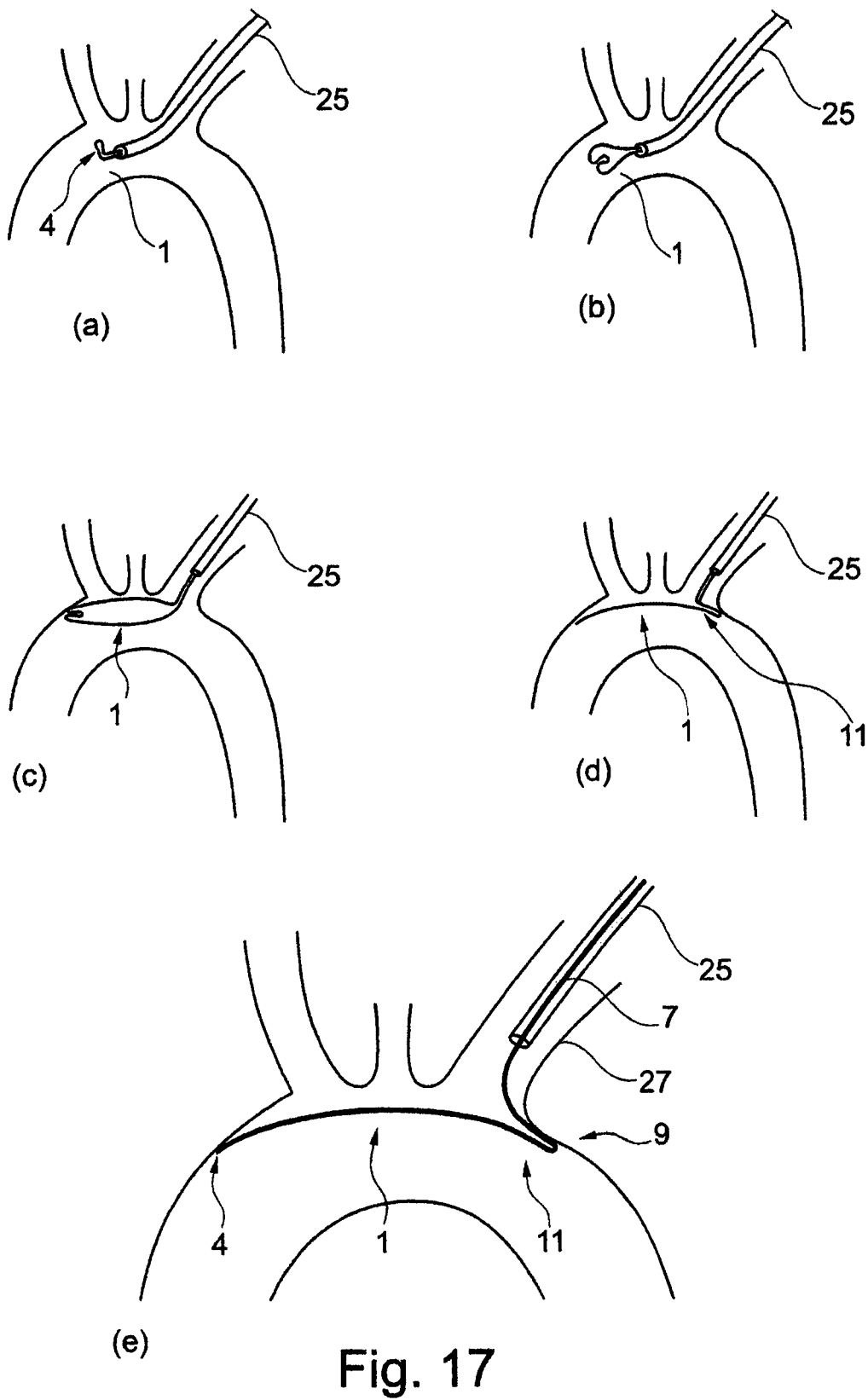
Figure 18:
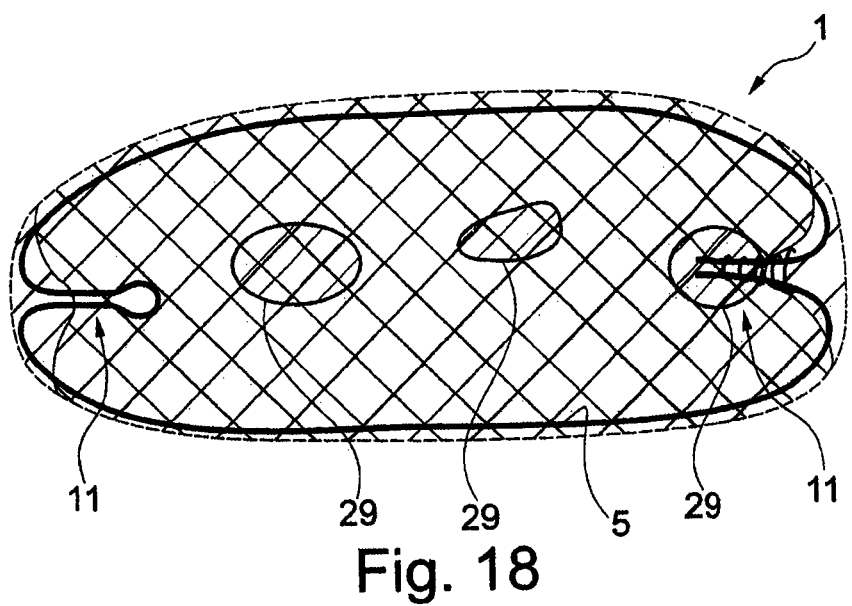
Figure 19:
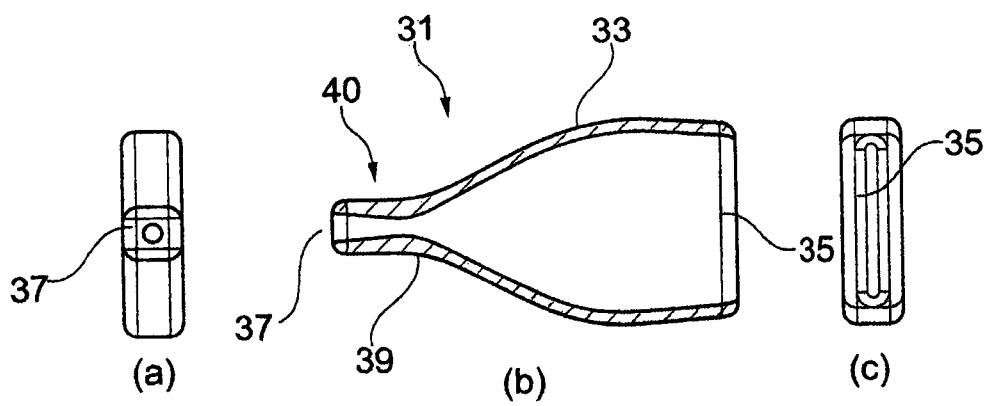
Figure 20:
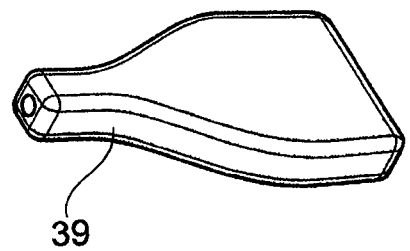
Figure 21:
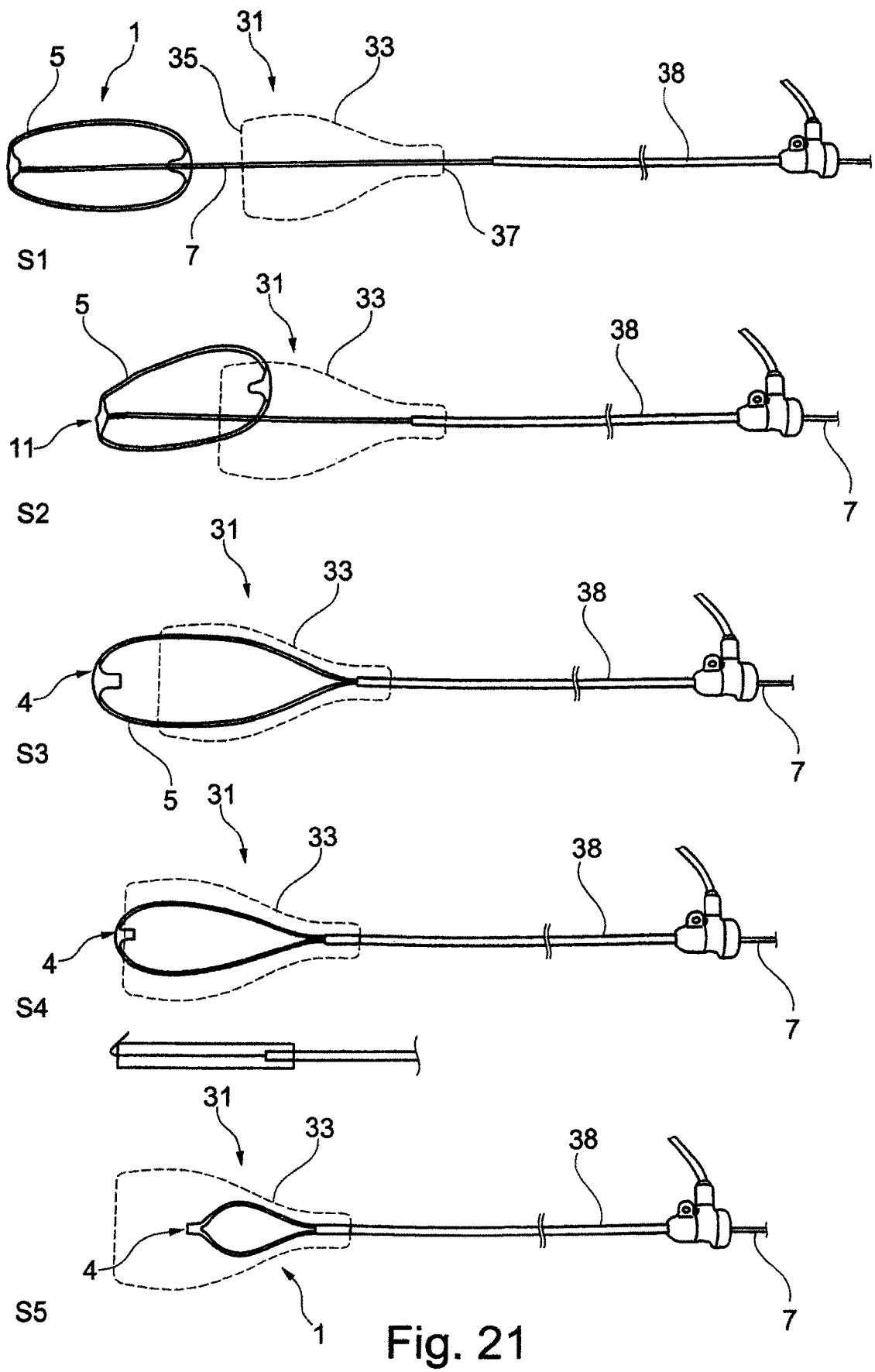

It is Shown, in:

FIG. 1: Embolic protection device according to the invention;

FIG. 2: Top view of the frame of the embolic protection device from FIG. 1;

FIG. 3: Side view of the frame from FIG. 2;

FIG. 4: Perspective view of the proximal area of the frame from FIG. 2;

FIG. 5A: Frame with a configuration of radiopaque markers;

FIG. 5B: Frame with a further configuration of radiopaque markers;

FIG. 6: Connection of an inventive proximal shape to the insertion device;

FIG. 7: Illustration of an adhesive tunnel in section with frame, filter unit and sealing;

FIG. 8: Top view of a frame with filter unit arranged at it;

FIG. 9: Distal filter unit from FIG. 8;

FIG. 10: Top view of a proximal shape with arranged filter unit;

FIG. 11: Perspective view of the proximal shape from FIG. 10;

FIG. 12: Top view of a distal shape with arranged filter unit;

FIG. 13: Perspective view of the distal shape from FIG. 12;

FIG. 14: View of a folded embolic protection device in a catheter;

FIG. 15A-F: Shaping of a frame of an inventive embolic protection device from a folded state to an unfolded state;

FIG. 16: Schematic view of an unfolded state of the embolic protection device after leaving a catheter;

FIG. 17: Sequence of the unfolding of an embolic protection device after leaving the catheter in an aortic arch;

FIG. 18: Covering of the head blood vessel outflows in the aorta due to the embolic protection device after leaving the catheter as in FIG. 17;

FIG. 19: Forming device for shaping an inventive embolic protection device;

FIG. 20: Perspective view of the forming device from FIG. 19;

FIG. 21: Method for folding the inventive embolic protection device by means of a forming device.

An embolic protection device 1 according to the invention is shown in FIG. 1. The embolic protection device 1 comprises a frame 5 to which a filter unit 3 is arranged. The frame 5 is connected to a feed unit 7. The length of the frame 5 is advantageously 50 to 100 mm. The width of the frame 5 is advantageously 15 to 45 mm. In this embodiment example, the frame 5 consists of a single continuously bent wire. However, the described characteristics and advantages of the embolic protection device also apply for other embodiment examples.

Frame 5 has a two-dimensional and a three-dimensional area. The two-dimensional area, that is the plane over which the frame spans, is oval in shape, which, at the distal and proximal areas 2, 9 changes into a proximal shape 11 and a distal shape 4. The proximal shape 11 and the distal shape 4 are the three-dimensional area of the frame 5, wherein the remaining areas of the frame 5 forms the two-dimensional area, that is, the oval shape. The embolic protection device 1 is shown in its basic state.

FIG. 2 shows a top view of the frame 5 of the embolic protection device 1 from FIG. 1. The proximal area 9 of the frame 5 is that which leads into the open ends 17, 19 of the frame 5, in this embodiment example the ends of the wire. The proximal area 9, and, therefore, also the proximal shape 11, is defined by the two loose ends 17, 19 of the frame 5 used or, respectively, the wire used. The proximal shape 11 has a first part 13 and a second part 15, which are formed in this embodiment by the parallel ends 17, 19. In the distal area 2, the frame 5 changes into a distal shape 4. The distal shape 4 has a constriction 12 of the wire of approximately 1-3 cm into the inside of the frame 5, or, expressed otherwise, into the inside of the oval, two-dimensional area.

In this embodiment example, the constriction 12 is a loop with a head diameter of about 1-1.8 mm and with the wire lying otherwise parallel to itself. The loop and the wire lying parallel to itself are located in the same two-dimensional plane of the frame 5.

FIG. 3 shows a side view of the frame 5 from FIG. 2. The proximal shape 11 is extended with the ends of the frame 17, 19 as well as the frame in the distal shape 4 mutually parallel into the inside of the frame 5. In this case, the first part 13 of the proximal shape is at a first angle W1 to the two-dimensional plane of the frame 5 of preferably 25 to 50 degrees downwards, wherein the angle is measured from the first part 13 to the plane of the frame. After preferably a length of 0.5 to 2.5 cm of the first part 13, a second part 15 is arranged on the end of the first part 13 at a second angle W2 of preferably 110 to 145 degrees upwards from the two-dimensional plane of the frame 5, wherein the angle is measured from the second part 15 to the plane of the frame. The length of the second part 15 is 1 to 5 cm. The lengths of the first and second part 13, 15 as well as their angle to the plane of the frame 5 may be selected larger or smaller corresponding to the requirements placed on the embolic protection device.

The first and second parts 13, 15 form the proximal shape 11, which is arranged in an inner area of the frame 5, wherein the proximal shape 11 extends over and under the plane of the frame 5. Due to this geometric shape of the proximal shape 11, the frame 5 is pretensioned and, at the same time, is stabilised in the longitudinal and lateral directions.

It is possible that the first part 13 extends into the plane of the frame 5, that is, the angle W1 equals 0 degrees and only the second part 15 is inclined to the plane of the frame 5 by a second angle W2.

The distal shape 4, comprising constriction 12, lies in the two-dimensional plane of the frame 5.

FIG. 4 shows a perspective view of the proximal area 9 of the frame from FIG. 2. The proximal shape 11 comprises the first part 13, which is bent by a first angle W1 to the plane of the frame 5, the second part 15 which is bent by a second angle W2 to the plane of the frame 5 and the two ends 17, 19 of the frame 5. Both the first part 13 as well as the second part 15 of the proximal shape 11 each have two frame wires.

FIGS. 5A and 5B show a frame 5 with a configuration of radiopaque markers 20. The radiopaque markers 20 are applied for radiopaque visibility on the frame 5 at prominent places. For example, the radiopaque markers 20 are applied in the area of the constriction 12 as well as on the frame in the distal area 2 so that the precise position of the tip of the frame 5 can be determined. Furthermore, radiopaque markers 20 are applied on the frame 5 outside the distal or proximal areas 2, 9. It is possible to determine in which state the folding or unfolding of the embolic protection device 1 is by the distance of the markers 20 from one another. Also, the precise position of the embolic protection device 1 in the aortic arch can be determined by means of the radiopaque markers 20.

The radiopaque markers can be sleeves made of platinum/ iridium, which are placed on or applied to the frame. The sleeves have a minimal greater internal diameter than the frame 5, have a wall thickness of about 50-100 μm and are attached by means of an adhesive.

In FIGS. 5A, 5B only some of the possible places for the positioning of radiopaque markers are shown. Furthermore, there are various possibilities for applying radiopaque markers 20 depending on the outcome desired.

FIG. 6 shows a connection of an inventive proximal shape 11 to an inventive feed device 7, wherein, in the drawing, the ends 17, 19 of the frame 5 the proximal shape 11 are shown. At the same time, the ends 17, 19 are also the end of the second part 15 of the proximal shape 11.

The feed unit 7 in this embodiment example comprises a stainless steel coil and the envelope is sealed. In this embodiment example, the outer diameter of the feed unit 7 is 1.5 mm and the diameter of its open lumen is 0.8 mm. The overall length of the feed unit 7 is 150 cm. Other dimensions for the feed unit 7 are possible.

The proximal shape 11 of the frame 5 is joined to the feed unit 7 by means of an adhesive unit 8, for example, polyurethane adhesive. The ends of the wire 17, 19 of the proximal shape 11 are pushed into the open inner lumen of the feed unit 7 and glued. For better visualisation, the adhesive unit 8 in the figure is cross hatched.

For additional stability, the ends of the wire 17, 19, that is, the second part 15 of the proximal shape 11, are secured by means of wrapped stainless steel wire 6. In this case, the ends of the wire 10 of the wrapped stainless steel wire 6 lie parallel to the ends 17, 19 of the frame 5, glued in the feed unit 7. The transition of the proximal shape 11 to the feed unit 7, as well as the wrapped stainless steel wire 6 are also coated with polyurethane in order to ensure a smooth surface as well as an even transition.

FIG. 7 shows an enlarged view of the connection of frame 5 and filter unit 3, shown in section. The connection is executed as an enveloping polymer shape around frame 5. The polymer shape forms an adhesive tunnel 41 in which the frame 5 is arranged on the filter unit 3. At the outer edge of the filter unit 3, the sealing 42 is shown in this figure.

FIG. 8 shows a top view over a frame 5 with a filter unit 3 arranged on it. The length of the frame 5 is advantageously 50 to 100 mm. The width of the frame 5 is advantageously 15 to 45 mm. The filter unit 3 in this embodiment example is secured to the frame 5 by means of an adhesive or by an adhesive based on polyurethane. The gluing runs continuously on the outer part of frame 5. The parts of the frame 5 in the proximal and distal areas, which, in the basic state, are folded inwards, are not glued to the filter unit 3. The filter unit 3 is glued from the lower side on to the frame 5 so that the surface of the filter unit 3 completely faces the central blood flow when frame 5 is positioned in its placement position in the aortic arch.

The frame 5, in this embodiment example made of nitinol, is glued in a prestressed manner to the filter unit 3 to achieve a better stretching force on the frame 5. In doing so, the width of the frame 5 is reduced from 35-45 mm to 25-35 mm.

The filter unit 3 projects with a protrusion 14 of about 1 mm over the frame 5 on its upper side and is turned over or flipped over in the distal and proximal areas 2, 9 of the frame 5 from the underside over the frame 5 to the upper side. The protrusion 14 of the attached filter unit 3 over the outer edge of the frame 5 has the additional function of a flexible sealing lip against the aorta wall when the embolic protection device 1 lies in the placement position in the aortic arch.

The flipped area of the filter unit 3 comprises a proximal filter unit 21 and a distal filter unit 22. The proximal and distal filter units 21, 22 are not glued to the frame which helps the desired deformation whenever it is pushed through a catheter. The proximal filter unit 21 together with the second part 15 of the proximal shape 11 is secured under the wrapped stainless steel wire 6 and is sealed in this area, as shown also in FIG. 7.

The distal filter unit 22 is secured at the constriction 12 of the distal shape 4. The distal filter unit 22 extends further over the constriction 12 towards the inside of the frame 5 by about 2-5 mm and is also flexibly sealed.

The fibres of the filter unit 3 are aligned such that they are aligned at an angle of 45° to the centre line of the frame 5 from the start to the end. This allows the filter unit 3 to extend better in the longitudinal direction while providing stability in the lateral direction. The outer edge of the protrusions 14 and 21 and 22 are also sealed.

FIG. 9 shows an end area of the distal filter unit 22 of the filter unit 3 from FIG. 8. The distal filter unit 22 is cut short such that it extends not only about 2 mm over the constriction 12, but becomes wider again beyond the constriction 12 and assumes the shape of a flag 23.

This flag 23 curls inwards. In doing so, the ends of the thread used for securing are trapped inside the flag 23. Glue secures the distal filter unit 23 from rolling up. The diameter of the curled distal filter unit 22 is less than 1.6 mm. Besides securing the distal filter unit 23, an additional protective pad is formed therefore between frame 5 and the aorta wall to avoid injuries.

FIG. 10 shows a top view over a proximal shape 11 with an arranged filter unit 3. The proximal filter unit 21 is flipped over the frame 5 to the upper side. In this embodiment example, both the first part 13 of the proximal shape 11 as well as the second part 15 of the proximal shape 11 are wrapped with a stainless steel wire 6 (For better visualisation of the stainless steel wire, the first and second parts 13, 15 of the proximal shape are not shown). The first part 13 is bent at a first angle W1 to the plane of the frame 5 and the second part 15 is bent at a second angle W2 to the plane of the frame 5.

FIG. 11 shows a perspective view of the proximal shape 11 from FIG. 10.

FIG. 12 shows a top view over a distal shape 4 with arranged filter unit 3, in particular a distal filter unit 22. The distal filter unit 22 is secured by means of a thread 43, which in other embodiments can be yarn or wire, at the constriction 12 of the distal shape 4 and projects into the inside of the frame 5.

FIG. 13 shows a top view over a proximal shape 11 with arranged filter unit 3. The flag 23 is rolled in, wherein a thread is used to secure it, as described for FIG. 9 and is not repeated here.

FIG. 14 shows a folded embolic protection device 1 in a catheter 25. The embolic protection device 1 is shown in a folded state. Due to mechanical shaping, the basic state of the embolic protection device, as shown, for example, in FIGS. 1 to 13, is changed to the folded state. The reversibly deformable material of the frame 5, for example, a superelastic nitinol wire, can be deformed such that the embolic protection device 1 can be pushed into a catheter 25. In doing so, the embolic protection device 1 extends lengthwise in its orientation. The distal shape 4 as well as the proximal shape 11 are folded into an outer area of the frame 5.

By folding the distal shape 4 and the proximal shape 11, the frame 5 transforms into a straight or extended shape. The change in length thus brought about depends on the reduction in the width of frame 5. The folded frame 5, i.e. the two sides of the frame outside the distal shape 4 and/or proximal shape 11, lie in this case parallel to each other in the catheter 25. The filter unit 3 can follow this mechanical deformation and is located in the intermediate space between catheter 25 and frame 5. In this extended shape, the embolic protection device can be pushed into a catheter with an inner diameter of, for example, 1.7 mm.

FIG. 15A-F shows shaping of a frame 5 of an inventive embolic protection device 1 from a folded state to an unfolded state.

When positioning the embolic protection device from a catheter 25, for example, in the aortic arch, the embolic protection device 1, in particular the frame 5 with the filter unit 3 arranged at it, is pushed out of the catheter 25. This is shown in FIGS. 15A-F.

The frame 5, which is formed from reversibly deformabable material, tries to revert to its original basic state, as shown, for example, in FIG. 1. The filter unit 3 arranged on frame 5 follows the reshaping. By feeding the folded distal shape 4 located in catheter 25 forward, on leaving catheter 25 with a feed of about 1-2 cm, up to a half of said shape folds back in the direction of the originally provided setting, as in FIG. 15A. In doing so, the direction of the distal shape 4 specifies in which position the embolic protection device 1 is located inside catheter 25. Radiopaque markers, which can be applied to the distal shape 4, enable the position of the distal shape 4 to be determined. In this case, the pointing direction of the distal shape 4 specifies the upper side of the embolic protection device 1. By rotating catheter 25, the placement position, for example, in the aortic arch, can be adjusted.

Figure 15A:
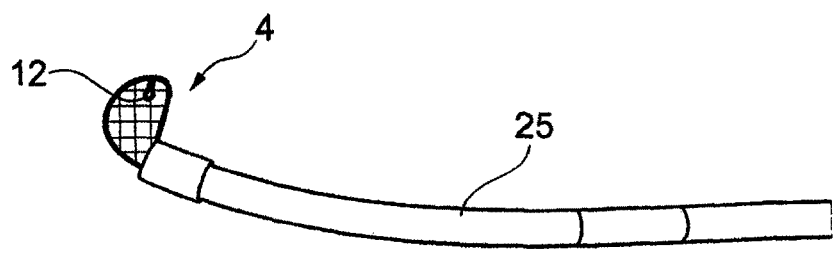
Figure 15B:
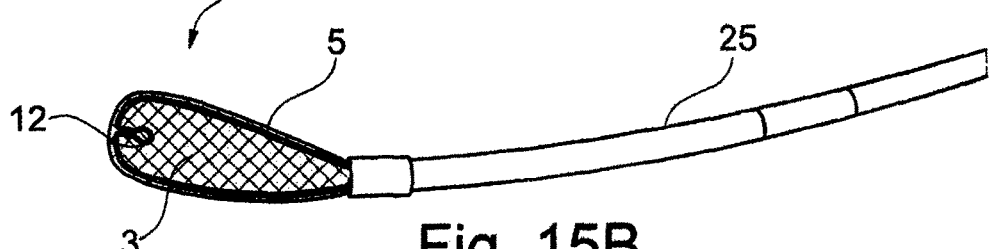

Since the constriction 12 in the distal area of the embolic protection device 1, that is, the distal shape 4 immediately after leaving catheter 25, unfolds, as in FIGS. 15A-B, the risk of possible damage to the wall of the blood vessel by feeding the embolic protection device 1 further is minimised. In addition, the frame 5 is wrapped on the distal shape 4 with atraumatic material which protrudes about 1-2 mm and, as a result, also counteracts any possible injuries.

Figure 15C:
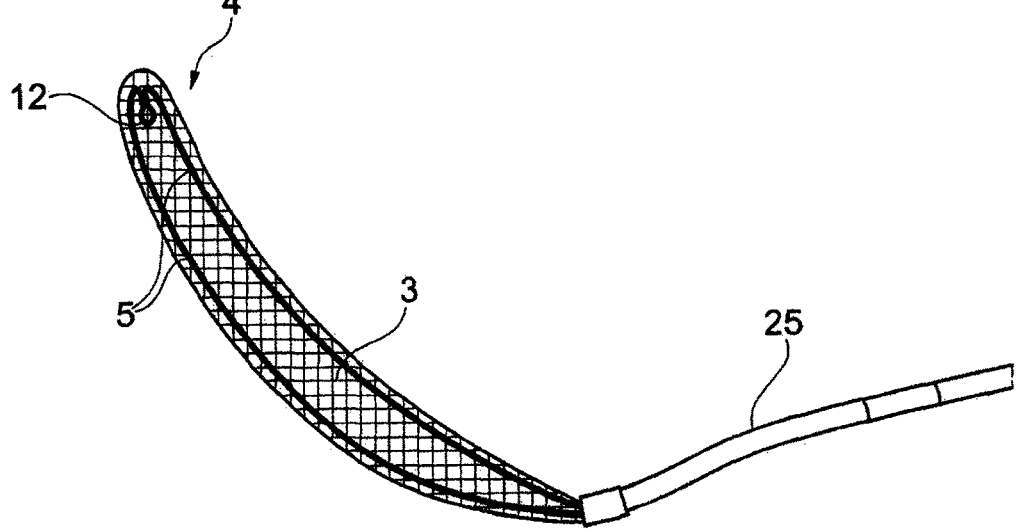
Figure 15D:
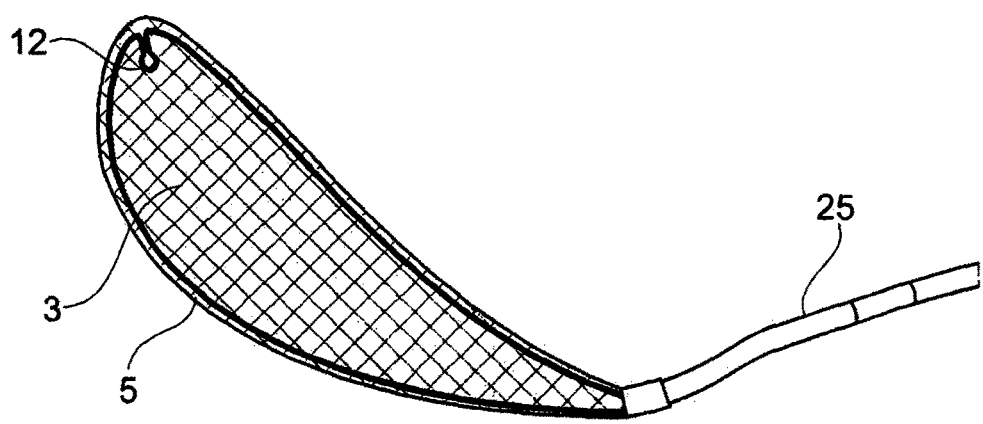

As the forward feed into the aortic arch continues, the frame 5 unfolds further until it is completely unfolded. This can be seen, for example, in FIGS. 15C-F. Here, FIG. 15D shows the same unfolded state as in FIG. 15C as seen from the side, wherein FIG. 15C shows the unfolded state as seen from above. Now almost completely unfolded, the distal shape 4 and the unfolded frame 5, as well as the unfolded filter unit 3 are shown.

Figure 15E:
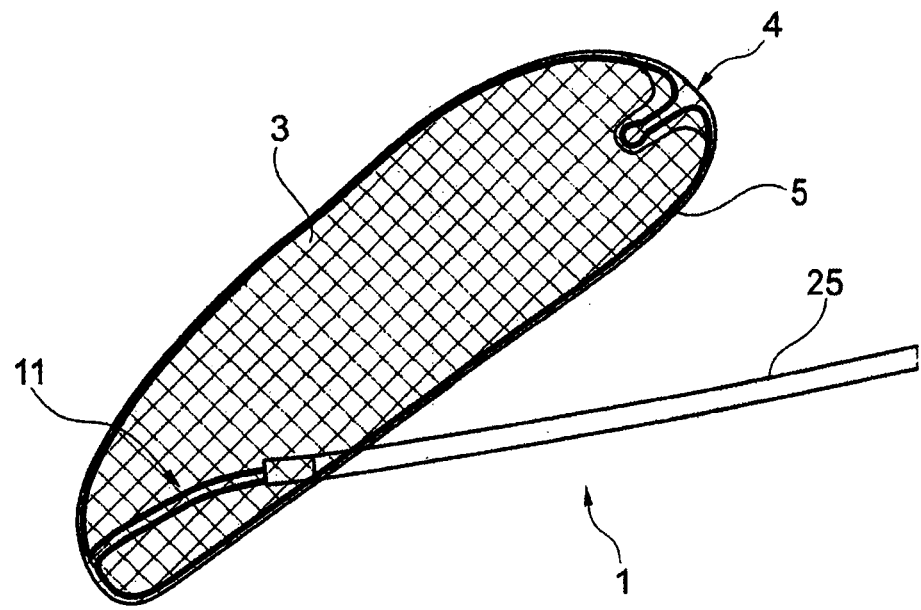
Figure 15F:
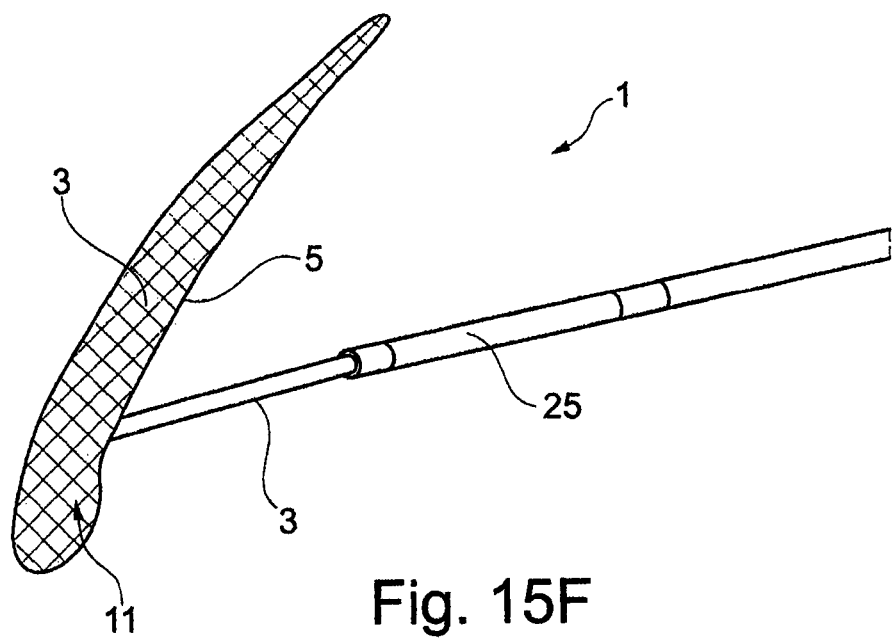

In the completely unfolded state, frame 5 is unfolded and the filter unit 3 is stretched out by frame 5. FIG. 15E shows the completely unfolded frame or unfolded embolic protection device 1 as seen from above and in FIG. 15F as seen from the side. The effect of the spring mechanism by the proximal shape 11 is evident from the transition from FIG. 15C to FIG. 15E or FIG. 15D to FIG. 15F.

FIG. 16 shows schematically an unfolded state of the embolic protection device 1 after leaving a catheter 25. Due to the special geometry of the proximal shape 11 up to the transition to the feed unit 3, a prestress is created on frame 5 to the same extent as the pre-bent proximal shape 11 is straightened. The figure shows two different conditions of the unfolded state. The position of the filter unit is the same in both illustrations. The position of the first and second parts 13, 15, which are connected to the feed unit (not shown), is shown both in the unstressed as well as the stressed state. As a result, a spring function is provided which will be explained more precisely below.

As soon as the embolic protection device 1 is correctly positioned, for example, in the aortic arch, the transferred tension of the proximal shape 11 presses the distal shape 4 to the aorta wall, thus providing a stable restraint against the blood flow—in FIG. 16 this is indicated schematically by the thick, short arrow on the distal shape 4. The proximal shape 11 moves in a direction which is indicated by the thin, curved arrow. Without the resistance of the aorta wall, frame 5 would follow the indicated folding direction—in FIG. 16 the thin, curved arrow—as shown, for example, in FIG. 15E-F. As shown in FIG. 16, the proximal shape 11 changes into a shape in which the first part 13 is at a first angle W1 of 25 to 50 degrees over the plane of the frame, measured from the plane to the first part 13 and the second part 15 is at an angle W2 of 30 to 110 degrees over the plane of the frame, measured from the second part 15 to the plane. The numbers of degrees given for the angle are dependent on the aorta geometry and are only by way of example.

FIG. 17 shows a schematic sequence of the unfolding of an embolic protection device 1 after leaving a catheter 25 in an aortic arch. In Figure part (a), the introduction of the catheter 25 through the left subclavian artery is shown, wherein the distal shape 4 of the embolic protection device 1 is at least partly folded back. Figure parts (b) to (d) show the further forward feed and the unfolding of the embolic protection device 1, wherein, in Figure part (d), the proximal shape 11 has also left the catheter. Figure part (e) shows the completely unfolded embolic protection device 1 in the placement state. In this process, the proximal area 9 of the frame 5 protrudes out over the area the ostium of the left subclavian artery, by means of which coverage over the entry way by the embolic protection device 1 is also achieved. At the same time, this protrusion offers a haptic feedback when positioning the embolic protection device: by pulling on the feed unit 7, a slight resistance can be felt as soon as the protrusion of the embolic protection device 1, or rather of the frame 5, is located correctly in front of the ostium 27. The intended position is achieved via the left subclavian artery in the aortic arch with the distal area 2 of the frame 5 towards the heart valve.

As an alternative entry way, the right subclavian artery can also be used. The sequence is similar to that shown in FIG. 16, but carried out in a mirrored manner. In this case, the distal area 2 of frame 5 points towards the descending aorta (descendens).

FIG. 18 shows the covering of the head blood vessel outflows 29 in the aorta by the embolic protection device 1 after leaving catheter 25 as in FIG. 17. Due to the special geometry of the frame 5, the embolic protection device 1 flexibly adapts to the anatomical conditions in the aortic arch independently of the entry way and offers a complete covering across all head blood vessels 29.

In the placement position in the aortic arch, the geometry of the frame 5 of the embolic protection device 1 flexibly adapts to the aorta wall and lies in a slight bow, following the bend in the aorta, in front of the head blood vessel outflows—as in FIG. 17(e) also. On leaving catheter 25, both the distal shape 4 as well as the proximal shape 11 fold back towards their original shape, that is, towards the inner area of frame 5, thus enabling an atraumatic positioning of the frame 5 to be made on the aorta wall. The folding avoids transitions with sharp edges or corners. Additional stabilisation of the frame 5 is achieved by the physiological conditions in the aorta, since the blood flow also presses the frame 5 of the embolic protection device 1 into its placement position.

FIG. 19 shows various views of a forming device 31 for shaping an inventive embolic protection device 1. In order to facilitate the shaping of the embolic protection device from an unfolded state in the basic state to a stretched state, the embolic protection device is retracted into the distal subsection 33 of the forming device 31. The distal subsection 33 of the forming device 31 has a flat funnel with a flat opening 35 about 25-40 mm wide and an opening height of about 3-10 mm. Along the length of the distal subsection 33 of the forming device 31 measuring about 60-80 mm, the opening area of the front face tapers to a narrow, circular cross section 39, with a diameter of approximately 1.7 mm. The proximal subsection 40 of the forming device 31 enlarges from the narrow cross section 39 to the round opening 37 with a diameter of about 1.8 to 5 mm diameter over a length of 20 to 40 mm. Thus, the overall length of the forming device 31 is 80 to 120 mm.

FIG. 20 shows a perspective view of the forming device 31 from FIG. 19.

FIG. 21 shows individual steps of the method for folding the inventive embolic protection device by means of a forming device 31, wherein the folded embolic protection device 1 is pushed into a substantially round tube 38, e.g. a commercially obtainable introducer sheath or a commercially obtainable catheter (with an internal diameter of 1.8 to 2.5 mm) 38. In a step S1, the frame 5 of the embolic protection device 1, with the feed unit 7 leading, is moved in front of the flat opening 35 of the forming device 31. In this process, the proximal end of the feed unit 7 is guided through the distal end of the forming device 31. The substantially circular tube 38 is pushed with its distal end on to the feed unit 7 proximally up to the front of the round opening 37 of the forming device 31, wherein the feed unit 7 protrudes out of this tube 38.

In a step S2, the tube 38 and the forming device 31 are connected together in the widened or conical round opening 37 of the forming device 31, for example, by a plug connection. By pulling on the feed unit 7, the embolic protection device 1 is straightened out.

By further pulling on the feed unit 7, in a step S3 the proximal shape 11 is folded on the outer edge of the distal subsection 33 of the forming device 31, so that it is stretched out as it is pulled through by the forming device 31.

Further pulling on the feed unit 7 in step S4 causes the distal shape 4 to be pushed over the outer edge of the distal subsection 33 of the forming device 31, wherein the distal shape 4 hooks on to the edge and is folded outwards. This is also emphasized in the side view of the figure.

In a step S5, the embolic protection device 1 is completely stretched out by retracting through the forming device 31. By pulling further on the feed unit 7, the sides of the frame 5 are pushed inwards until the entire frame, elongated, is pulled into the tube 38. The embolic protection device 1 remains in this tube 38. The forming device 31 can now be removed from the tube 38.

In summary, it is maintained that, by means of the described methods, an inventive embolic protection device (1) is specified for insertion into an aortic arch, comprising a filter unit (3), a frame (5) and a feed unit (7), wherein the filter unit (3) is arranged on the frame (5) and the frame (5) has a proximal area (9), which comprises a proximal shape (11), which is arranged in an inner area of the frame (5) and is connected to the feed unit (7), wherein the proximal shape (11) comprises a first part (13) and a second part (15), wherein the second part (15) is formed at one end of the first part (13).

In a further development of the embolic protection device (1), the first part (13) of the proximal shape (11) is at a first angle (W1) to the plane of the frame (5) and the second part (15) is at a second angle (W2) to the first part (13) of the proximal shape (11).

According to the invention, an embolic protection device (1) is provided for insertion into an aortic arch, comprising a filter unit (3), a frame (5) and a feed unit (7), wherein the filter unit (3) is arranged on the frame (5) and the frame (5) has a proximal area (9), which comprises a proximal shape (11), which is arranged in an inner area of the frame (5) and is connected to the feed unit (7), wherein the proximal shape (11) comprises a first part (13) and a second part (15), wherein the first and second parts (13, 15) are arranged together such that they form a spring mechanism.

In a further development of the embolic protection device (1), the proximal shape (11) can be set under tension by the feed unit (7).

In a further development of the embolic protection device (1), the proximal shape (11) comprises two ends (17, 19) of the frame (5), which extend parallel to each other in the inner area of the frame (5).

In a further development of the embolic protection device (1), the proximal shape (11) is connected to the feed unit (7), wherein the two ends (17, 19) of the frame (5) are wrapped by a wire (6), whose ends (10) are arranged parallel to the ends (17, 19) of the frame (5).

In a further development of the embolic protection device (1), the frame (5) has a distal area (2) which comprises a distal shape (4), which is arranged in an inner area of the frame (5).

In a further development of the embolic protection device (1), the distal shape (4) has a constriction (12) towards the inside of the frame (5).

In a further development of the embolic protection device (1), the connection of frame (5) and filter unit (3) is carried out by means of an adhesive tunnel or an adhesive tunnel connection.

In a further development of the embolic protection device (1), the filter unit (3) is connected with the frame (5) outside the proximal and/or distal area(s) (9, 2).

In a further development of the embolic protection device (1), the filter unit (3) is connected to the frame (5) in the distal area (2) substantially up to the start of the distal shape (4).

In a further development of the embolic protection device (1), the filter unit (3) is connected to the frame (5) in the proximal area (2) substantially up to the first part (13) of the proximal shape (11).

In a further development of the embolic protection device (1), is the filter unit (3) is connected flexibly to the frame (5) in the distal and proximal areas (2, 9).

In a further development of the embolic protection device (1), the frame (5) is connected to the filter unit (3) with prestress in the lateral direction.

In a further development of the embolic protection device (1), the filter unit (3) has a protrusion (14) over the frame (5).

In a further development of the embolic protection device (1), the protrusion (14) is sealed.

In a further development of the embolic protection device (1), the protrusion (14) is formed as a sealing lip.

In a further development of the embolic protection device (1), in the proximal and/or distal area(s) (9, 2) of the frame (5) the filter unit (3) is flipped over the frame (5) from the lower side to the upper side.

In a further development of the embolic protection device (1), the filter unit (3) is secured by means of a thread, wire or yarn to the distal shape (4).

In a further development of the embolic protection device (1), the securing of the filter unit (3) by means of a thread, wire or yarn to the distal shape (4) is sealed.

In a further development of the embolic protection device (1), the filter unit (3) is secured by means of gluing to the distal shape (4).

In a further development of the embolic protection device (1), the filter unit (3) is secured by means of a coil in the proximal area (9).

In a further development of the embolic protection device (1), the filter unit (3) has a fibre material, wherein the fibres are aligned such that they make an angle of substantially 45 degrees to a longitudinal axis of the frame (5).

In a further development of the embolic protection device (1), the frame (5) has a basic state in the form of an oval shape.

According to the invention, a forming device (31) is specified for reshaping the embolic protection device (1) for insertion into a tube, wherein a frame (5), with a filter unit (3) arranged on it, of the embolic protection device (1) is deformed from an expanded state to a stretched state, comprising on one side a flat or round opening (35), a narrowest cross section (39) and a round opening (37) at the opposite end.

In a further development of the forming device, the flat or round opening (35) of the forming device (31) is formed such that the proximal shape (11) and/or the distal shape (4) of the frame (5) of the embolic protection device is folded outwards.

According to the invention, a method is specified for folding the embolic protection device by means of the forming device, comprising pushing (S1) the frame (5) of the embolic protection device in front of the flat or round opening (35) of the forming device (31), wherein the feed unit (7) is fed through the forming device (31), drawing (S3) the proximal shape (11) into the forming device (31), wherein the proximal shape (11) is folded outwards, the distal shape (4) hooks (S4) over the outer edge of the forming device (31), and by pulling the distal shape (4) folded outwards further, it is drawn into the forming device (31).

In a further development of the method, due to the frame (5) being pulled into the forming device (31), the frame (5) is stretched out lengthwise.

In a further development of the method, wherein the folded proximal shape (11) transfers a prestress to the frame (5), which is substantially equal to the tension resulting from it, the curved proximal shape (11) is straightened.

According to the invention, a method for unfolding the embolic protection device is specified when the embolic protection device leaves a catheter containing it, comprising pushing the embolic protection device out of the catheter, folding the distal shape (4) back into an inner area of the frame (5), when a distal area (2) of the frame of the embolic protection device leaves the catheter.

A further development of the method comprises indicating the direction of the frame (5) by means of one or a multiplicity of markers, when the distal area (2) leaves the catheter, wherein the distal area (2) specifies the orientation of the frame (5).

A further development of the method wherein, due to the prebending of the distal shape as well as the proximal shape, torsion is generated in the wire of the frame (5), the preferred direction of which, when leaving the catheter, is towards the curved tip of the distal shape.

REFERENCE LIST

1 Embolic protection device
2 Distal area
3 Filter unit
4 Distal shape
5 Frame
6 Stainless steel wire
7 Feed unit
8 Adhesive unit
9 Proximal area
10 Ends of the wire
11 Proximal shape
12 Constriction
13 First part
14 Protrusion
15 Second part
17, 19 Ends of the frame
20 Marker
21 Proximal filter unit
22 Distal filter unit
23 Flag
25 Catheter
27 Ostium
29 Head blood vessel outflows
31 Forming device
33 Distal subsection
35 Flat opening
37 Round opening
38 Tube
39 Very narrow cross section
40 Proximal subsection
41 Adhesive tunnel
42 Sealing
43 Thread
S1-S5 Method steps
W1 First angle
W2 Second angle

The invention claimed is:

1. Embolic protection device (1) for insertion into an aortic arch, comprising
   a filter unit (3),
   a frame (5) with a proximal end and a distal end and
   a feed unit (7) located at the proximal end of the frame,
   wherein the filter unit (3) is arranged within the frame (5) and the frame (5) is comprised of a wire and provides a proximal area (9), comprising a proximal shape (11) and provides a distal area (2) comprising a distal shape (4),
   wherein the frame (5) defines a generally oval two-dimensional area,
   where the proximal shape (11) is arranged at the proximal end of the frame (5) and is connected to the feed unit (7),
   wherein the proximal shape (11) comprises a first part (13) and a second part (15),
   wherein the second part (15) is formed at one end of the first part (13) and the second part is connected to the feed unit,
   wherein the first and second parts (13, 15) form the proximal shape (11), wherein the proximal shape (11)

extends over and under the generally oval two-dimensional area of the frame (5), and wherein the distal shape (4) has a constriction (12) of the wire of the frame (5) into an interior of the generally oval two-dimensional area of the frame (5).

2. Embolic protection device (1) according to claim 1, characterized in that the first part (13) of the proximal shape (11) is at a first angle (W1) to the generally oval two-dimensional area of the frame (5) and the second part (15) is at a second angle (W2) to the first part (13) of the proximal shape (11).

3. Embolic protection device (1) for insertion into an aortic arch, comprising
a filter unit (3),
a frame (5) with a proximal end and a distal end and
a feed unit (7) located at the proximal end of the frame,
wherein the filter unit (3) is arranged within the frame (5) and the frame (5) is comprised of a wire and has a proximal area (9), comprising a proximal shape (11) and a distal area (2) comprising a distal shape (4), wherein the frame (5) defines a generally oval two-dimensional area, where the proximal shape (11) is arranged at the proximal end of the frame (5) and is connected to the feed unit (7)
wherein the proximal shape (11) comprises a first part (13) and a second part (15),
wherein the first and second parts (13, 15) form the proximal shape (11),
wherein the proximal shape (11) extends over and/or under the generally oval two-dimensional area of the frame (5),
wherein the second part is formed at one end of the first part (13) and the second part is connected to the feed unit,
wherein the first and second parts (13, 15) are arranged to each other such that they form a spring mechanism, and
wherein the distal shape (4) has a constriction (12) of the wire of the frame (5) into an inside of the generally oval two-dimensional area of the frame (5).

4. Embolic protection device (1) according to any one of claims 1-3, characterized in that the proximal shape (11) can be set under tension via the feed unit (7).

5. Embolic protection device (1) according to claim 1, characterized in that the proximal shape (11) comprises two ends (17, 19) of the frame (5), which extend parallel to each other.

6. Embolic protection device (1) according to claim 1, characterized in that the filter unit (3) is connected to the frame (5) outside the proximal and/or distal area(s) (9, 2).

7. Forming device (31) for shaping the embolic protection device (1) according to claim 1 for insertion into a tube (38), wherein the frame (5) of the embolic protection device (1) having the filter unit (3) arranged at it, is formed from an expanded state to a stretched state, comprising a one-sided flat or round opening (35), a narrowest cross section (39)' and an opposite round opening (37).

8. Forming device (31) according to claim 7, wherein the flat or round opening (35) of the forming device (31) is formed such that at least one of the proximal shape (11) and the distal shape (4) of the frame (5) of the embolic protection device is folded outwards.

9. Method for folding the embolic protection device by means of the forming device according to claim 7, comprising
moving (S1) the frame (5) of the embolic protection device in front of the flat or round opening (35) of the forming device (31),
wherein the feed unit (7) is fed through the forming device (31),
retracting (S3) the proximal shape (11) into the forming device (31),
wherein the proximal shape (11) is folded outwards, the distal shape (4) hooks (S4) over the outer edge of the forming device (31), and by pulling the distal shape (4) further is folded outwards, and is retracted into the forming device (31).

10. Method according to claim 9, wherein the folded proximal shape (11) transfers a prestress to the frame (5), which is substantially equal to the tension resulting from straightening the folded proximal shape (11).

11. Method for unfolding the embolic protection device according to claim 1, when the embolic protection device leaves a catheter containing it, comprising
pushing the embolic protection device out of the catheter, folding the distal shape (4) into the distal end of the frame (5) when the distal area (2) of the frame of the embolic protection device leaves the catheter.

12. Method according to claim 11, comprising indicating the direction of the frame (5) by a marker, when the distal area (2) leaves the catheter, wherein the distal area (2) indicates the orientation of the frame (5).

13. Method according to claim 11, characterised in that, due to the folding of the distal shape, as well as the proximal shape, a torsion is generated in the wire of the frame (5), having a preferred direction, when leaving the catheter, from the distal area (2) towards the distal shape (4).

14. Embolic protection device (1) according to claim 1, wherein the proximal shape (11) is defined by two ends (17, 19) of the frame (5).

15. Embolic protection device (1) according to claim 3, wherein the proximal shape (11) is defined by two ends (17, 19) of the frame (5).

* * * * *